United States Patent [19]

Vigouret

[11] Patent Number: 4,795,759
[45] Date of Patent: Jan. 3, 1989

[54] USE OF DIBENZ(CD,F)INDOLES

[75] Inventor: Jean-Marie Vigouret, Alle, Switzerland

[73] Assignee: Sandoz Ltd., Basel, Switzerland

[21] Appl. No.: 888,920

[22] Filed: Jul. 23, 1986

[30] Foreign Application Priority Data

Jul. 27, 1985 [DE] Fed. Rep. of Germany ....... 3527045
Jul. 27, 1985 [DE] Fed. Rep. of Germany ....... 3527044

[51] Int. Cl.$^4$ .............................................. A61K 31/40
[52] U.S. Cl. .................................................... 514/429
[58] Field of Search ......................................... 514/429

[56] References Cited

U.S. PATENT DOCUMENTS 4,602,032  7/1986  Giger .................................. 514/410

FOREIGN PATENT DOCUMENTS 2024818   1/1980  United Kingdom .
2078225A  1/1982  United Kingdom .

OTHER PUBLICATIONS

Chem. Abst. 103-71188y (1985).

Primary Examiner—Stanley J. Friedman
Attorney, Agent, or Firm—Gerald D. Sharkin; Robert S. Honor; Thomas O. McGovern

[57] ABSTRACT 4,5,5a,6-tetrahydro-dibenz[cd,f]indole derivatives having at least one oxy substitutent in one or both of the fused benzene rings, for the prevention of alcohol abuse.

10 Claims, No Drawings

USE OF DIBENZ(CD,F)INDOLES

The present invention relates to a new pharmaceutical use of dibenz[cd,f]indoles.

More particularly the present invention relates to a new pharmaceutical use for 4,5,5a,6-tetrahydrodibenz[cd,f]indole derivatives having at least one oxy substituent in one or both of the fused benzene rings and pharmaceutically acceptable acid addition salts thereof, hereinafter referred to as compounds for use according to the invention.

In accordance with the present invention it has now surprisingly been found that compounds for use according to the invention are useful for preventing alcohol abuse.

Alcohol abuse, or excessive alcohol consumption comprises acute alcohol intoxication and chronic alcohol abuse with or without dependence, and is a well known, major medical and social problem. Medical complications (e.g. gastritis, liver cirrhosis, fatty liver disease, etc.) comprise only one element of alcohol abuse. Social, legal, financial and vocational deterioration often occurs as compulsive alcohol use becomes the user's highest priority.

Abrupt cessation of chronic high-dose of alcohol can result in a variety of undesirable physical symptoms, e.g. alcohol craving, tremor, nausea, malaise, anxiety, depression etc. up to delirium tremens and seizures.

If one excludes the deterrent approach, which consists in using substances that deter the patient from using the causative agent (alcohol) e.g. by inducing emesis, there exists, apart from acute detoxification, no established drug treatment to prevent alcohol abuse. After acute detoxification, intervention is mainly psychosocial, and most rehabilitation programmes do not recourse to medications.

Although clinicians often do prescribe drugs, especially anxiolytics and antidepressants, this is in fact an empirical approach for the symptomatic treatment of alcoholism.

On the other hand, there is some evidence from recent clinical trials that apomorphine and bromocriptine can reduce alcohol dependence as well as improve anxiety, sleep disturbances and depressive symptoms [V. Borg et al., Curr. Ther. Res. 27, 170–177 (1980)]. However these compounds induce a concomitant reduction of food and liquid ingestion, resulting in loss of body weight.

In the present invention it has been found that alcohol abuse can be prevented by administering to an alcohol abuser a therapeutically effective amount of a compound for use according to the invention.

Moreover it has surprisingly been found that these compounds do not induce a concomitant reduction of food and liquid ingestion.

The oxy substituent(s) in the compounds for use according to the invention may be for example hydroxy or a group which is hydrolysable under physiological conditions to a hydroxy group, e.g. an acyloxy group. Alternatively it may be an ether group. Conveniently the 4 position is substituted, e.g. by a cycloalkyl or alkyl radical.

Conveniently the compounds for use according to the invention contain up to 4, preferably 2 oxy substituents.

Conveniently the oxy substituents are in the 9 and/or 10 positions.

The preferred compounds for use according to the invention are of formula I,

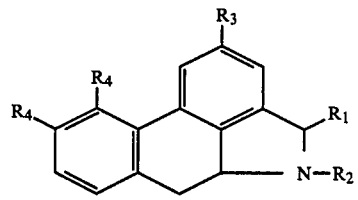

wherein
$R_1$ is hydrogen, $(C_{1-10})$alkyl, $(C_{3-7})$cycloalkyl or $(C_{3-7})$cycloalkyl-$(C_{1-4})$alkyl,
$R_2$ is $(C_{1-5})$alkyl,
$R_3$ is $(C_{1-4})$alkyl and
the $R_4$ substituents are the same and are hydroxy or acyloxy radicals, in free base form or in pharmaceutically acceptable acid addition salt form.

$R_1$ is preferably an alkyl radical. When $R_1$ is an alkyl radical, this contains conveniently 1 to 6 carbon atoms and may for example signify methyl.

Conveniently, $R_2$ is an alkyl radical containing 1 to 4 carbon atoms.

$R_3$ is preferably methyl.

The $R_4$ substituents are preferably hydroxy radicals. When the $R_4$ substituents are acyloxy radicals, these may be radicals of formula $R_a$—CO—O— in which $R_a$ is unsubstituted or substituted alkyl; $(C_{3-7})$cycloalkyl; an unsubstituted or substituted phenyl radical, or a 5- or 6-membered heterocyclic ring.

Preferably $R_a$ is $(C_{1-7})$alkyl; $(C_{3-6})$cycloalkyl; unsubstituted phenyl; phenyl mono- or disubstituted by chlorine, fluorine, trifluoromethyl, $(C_{1-4})$alkyl or $(C_{1-4})$alkoxy; unsubstituted benzyl; or benzyl mono- or disubstituted by chlorine, fluorine, $(C_{1-4})$alkyl or $(C_{1-4})$alkoxy.

The compounds (−)-(4S,5aR)-5-ethyl-4,5,5a,6-tetrahydro-9,10-dihydroxy-4-n-propyl-dibenz[cd,f]indole and (−)-(4S,5aR)-5-ethyl-4,5,5a,6-tetrahydro-9,10-dihydroxy-2-methyl-4-n-propyl-dibenz[cd,f]indole, in free base form or in pharmaceutically acceptable acid addition salt form, are particularly preferred.

The compounds for use according to the invention and their preparation are described for example in the British patent application Ser. Nos. 79 21 344, 81 19 500 and 83 09 728. They are known to exhibit central dopaminergic activity and are therefore indicated e.g. for the treatment of Parkinson's disease.

The administered amount of compound for the new use according to the invention will vary depending on the active agent used and the patient undergoing treatment. In general the therapeutically effective amount of compound for use according to the invention is from 0.05 to 50 mg per day.

The compound can be administered on a set schedule, for example every 4 to 6 hours, or it can be administered in accordance with the patient's requirement. The compound is conveniently administered in unit doses of about 0.01 to 25 milligrams 2 to 4 times daily, preferably about 0.5 to 5 milligrams 2 to 3 times daily.

When appropriate, the compound for use according to the invention may be employed in free base form or in pharmaceutically acceptable salt form. The compounds of formula I may, for example, be used in the form of the hydrochloride salt. Generally the activities of such salt forms will be of the same order as those of the respective free forms.

The compounds for use according to the invention may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. Tablets may contain the compounds for use according to the invention in admixture with conventional pharmaceutically acceptable excipients, e.g., inert diluents and granulating, disintegrating and lubricating agents. The tablets may be uncoated or coated by known techniques to delay disintegration and absorption in the gastrointestinal tract and thereby provide a sustained action over a longer period. Similarly, suspensions, syrups and elixirs may contain the compounds for use according to the invention in admixture with any of the conventional excipients utilized in the preparation of such compositions. Capsules may contain the active ingredients alone or admixed with an inert solid diluent. The injectable compositions are formulated as known in the art. These pharmaceutical preparations may contain up to about 90% of the compounds for use according to the invention in combination with the carrier or adjuvant.

In one preclinical trial, (−)-(4S,5aR)-5-ethyl-4,5,5a,6-tetrahydro-9,10-dihydroxy-4-n-propyl-dibenz[cd,f]indole was tested in alcohol preferring rats.

Male and female rats of an alcohol preferring strain were placed in individual cages each containing an eatometer according to Fallon [Science 148, 977–8 (1965)] and two bottles fitted with double sphere valves, allowing a gravimetric determination of the quantities of food and beverage actually taken. The animals received a vitamin rich standard chow, distilled water in one bottle and an aqueous ethanol solution (10% per volume) in the other. Under these conditions 50 to 97% of the absorbed liquid was taken from the bottle containing the ethanol solution, which corresponds to a daily consumption of 4 to 6 g pure ethanol by kg animal body weight, and the rats developed an ethanol addiction which appeared from their increasing startle behaviour when shaking the cages during the abstinence periods.

The compound was administered p.o in aqueous solution and the consumption of food, water and alcohol was recorded during 12 hours and compared with the average consumption within a period of 3 days before the administration.

The following results were obtained:

| Dose (mg/kg p.o.) | N | ΔL | ΔEtOH | ΔF |
|---|---|---|---|---|
| Controls | 9 f | +2.0 | +5.1 | +0.2 |
| 0.5 | 8 m | −4.1 | −47.2 | +8.6 |
| 1 | 14 m | −18.2 | −43.8 | −0.6 |
| 1 | 9 m | −22.7 | −40.1 | −4.4 |
| 1 | 8 m | −11.8 | −63.0 | −6.5 |
| 2 | 14 m | −25.3 | −64.4 | −10.0 |
| 2 | 10 f | −12.8 | −81.5 | −14.8 |

N: Number and sex of animals (m = male, f = female)
ΔL: Change in % of total liquid consumption (+ = increase, − = decrease)
ΔEtOH: Change in % of pure ethanol consumption (+ = increase, − = decrease)
ΔF: Change in % of food consumption (+ = increase, − = decrease)

The results of the study show that alcohol consumption is significantly reduced by the administration of the active agent without significant reduction of food and liquid ingestion.

The present invention also provides a method of preventing alcohol abuse, which comprises administering to a subject in need of such treatment a 4,5,5a,6-tetrahydro-dibenz[cd,f]indole derivative having at least one oxy substituent in one or both of the fused benzene rings or an acid addition salt thereof in an amount effective to prevent alcohol abuse.

The present invention further provides a pharmaceutical composition which incorporates a 4,5,5a,6-tetrahydro-dibenz[cd,f]indole derivative having at least one oxy substituent in one or both of the fused benzene rings or an acid addition salt thereof for use in the prevention of alcohol abuse.

Gelatine capsules having the following composition may be prepared according to conventional methods and are suitable for use in the treatment of alcohol abuse:

| | |
|---|---|
| (−)-(4S,5aR)-5-ethyl-4,5,5a,6-tetrahydro-9,10-dihydroxy-4-n-propyl-dibenz[cd,f]indole-chlorhydrate | 1.118 mg* |
| Lactose | 173.182 mg |
| Silicium dioxide (Aerosil 200) | 1.5 mg |
| Corn starch | 120.0 mg |
| Maleic acid | 1.2 mg |
| Magnesium stearate | 3.0 mg |
| total | 300.0 mg |
| empty capsule | 77.0 mg |
| final weight | 377.0 mg |

*1 mg base corresponds to 1.118 mg chlorhydrate

What we claim is:

1. A method of preventing alcohol abuse which comprises administering to a subject in need of such treatment a therapeutically effective amount of a 4,5,5a,6-tetrahydro-dibenz[cd,f]indole derivative having at least one oxy substituent in one or both of the fused benzene rings, or a pharmaceutically acceptable acid addition salt thereof.

2. A method of preventing alcohol abuse which comprises administering to a subject in need of such treatment a pharmaceutically acceptable 4,5,5a,6-tetrahydrodibenz[cd,f]indole derivative having at least one hydroxy, ether or physiologically hydrolysable acyloxy substituent in one or both of the fused benzene rings, or a pharmaceutically acceptable acid addition salt thereof in an amount effective for preventing alcohol abuse.

3. A method of preventing alcohol abuse which comprises administering to a subject in need of such treatment a pharmaceutically acceptable 4,5,5a,6-tetrahydrodibenz[cd,f]indole derivative having a hydroxy substituent in the 9- and 10-position, or a pharmaceutically acceptable acid addition salt thereof in an amount effective for preventing alcohol abuse.

4. A method of preventing alcohol abuse according to claim 2, which comprises administering to a subject in need of such treatment a compound of formula I

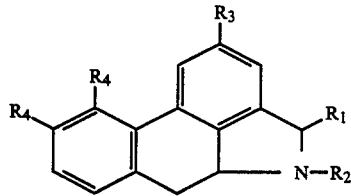

wherein
$R_1$ is hydrogen $(C_{1-10})$alkyl, $(C_{3-7})$cycloalkyl or $(C_{3-7})$cycloalkyl-$(C_{1-4})$alkyl,
$R_2$ is $(C_{1-5})$alkyl,
$R_3$ is $(C_{1-4})$alkyl and
the $R_4$ substituents are the same and are hydroxy or acyloxy radicals,
in free base form or in pharmaceutically acceptable acid addition salt form, in an amount effective for preventing alcohol abuse.

5. A method according to claim 3, in which the active agent is (−)-(4S,5aR)-5-ethyl-4,5,5a,6-tetrahydro-9,10-dihydroxy-4-n-propyl-dibenz[cd,f]indole or a pharmaceutically acceptable acid addition salt thereof.

6. A method according to claim 4, in which the active agent is (−)-(4S,5aR)-5-ethyl-4,5,5a,6-tetrahydro-9,10-dihydroxy-2-methyl-4-n-propyl-dibenz[cd,f]indole or a pharmaceutically acceptable acid addition salt thereof.

7. A method according to claim 1, in which 0.05 to 50 mg of the active agent is administered per day.

8. A method according to claim 1, in which the active agent is administered in a unit dose of from 0.01 to 25 milligrams.

9. A method according to claim 1, in which the active agent is administered in a unit dose of from 0.01 to 10 milligrams.

10. A method according to claim 1, in which the active agent is administered in a unit dose of from 0.5 to 5 milligrams.